United States Patent [19]

Schütze et al.

[11] Patent Number: 4,892,950

[45] Date of Patent: Jan. 9, 1990

[54] PROCESS FOR THE PREPARATION OF NAPHTHALENE-1,8-DICARBOXIMIDES

[75] Inventors: Detlef-Ingo Schütze, Cologne; Klaus Wunderlich, Leverkusen; Karl-Heinz Reinhardt, Leverkusen; Martin Wienkenhöver, Leverkusen, all of Fed. Rep. of Germany

[73] Assignee: Bayer Aktiengesellschaft, Leverkusen, Fed. Rep. of Germany

[21] Appl. No.: 204,468

[22] Filed: Jun. 9, 1988

[30] Foreign Application Priority Data

Jun. 13, 1987 [DE] Fed. Rep. of Germany ....... 3719850

[51] Int. Cl.$^4$ ............................................ C07D 221/14
[52] U.S. Cl. ....................................... 546/98; 546/99; 546/100
[58] Field of Search ............................ 546/96, 99, 100

[56] References Cited

U.S. PATENT DOCUMENTS 3,929,771 12/1975 Austin .................................. 546/100
4,007,192 2/1977 Fuchs ................................... 546/98

*Primary Examiner*—Mark L. Berch
*Attorney, Agent, or Firm*—Sprung Horn Kramer & Woods

[57] ABSTRACT

Process for the preparation of naphthalene-1,8-dicarboximide which is optionally substituted in the naphthalene ring, characterized in that naphthalene-1,8-dicarboxylic anhydride which is optionally substituted in the naphthalene ring is reacted with an ammonium salt in an aqueous medium at a pH near to the neutral point, the reaction mixture is then acidified to a pH of 1 to 4 and the pH is subsequently adjusted to a value near to the neutral point.

6 Claims, No Drawings

PROCESS FOR THE PREPARATION OF NAPHTHALENE-1,8-DICARBOXIMIDES

This invention relates to a process for the preparation of naphthalene-1,8-dicarboximide which is optionally substituted in the naphthalene ring.

Naphthalene-1,8-dicarboximides are important dyestuff intermediate products. In particular, unsubstituted naphthalene-1,8-dicarboximide is a valuable intermediate product for the preparation of perylenetetracarboxylic acid diimide, which, in turn, by saponification to give perylenetetracarboxylic dianhydride or directly, constitutes the basis for the synthesis of perylenetetracarboxylic acid pigments.

A process for the preparation of naphthalene-1,8-dicarboximide and its derivatives which has been known for a fairly long time starts from naphthalene-1,8-dicarboxylic anhydride, which is reacted in aqueous ammonia. A large excess of ammonia is required in this reaction in order to achieve high yields (see, for example, Chem. Zentralblatt 1959, page 2432: Abstract of J. allg. Chem. (Russian) 28 (90), 692–695, March 1958). In addition it is necessary for the naphthalene-1,8-dicarboxylic anhydride employed to be free from naphthalic acid, since the latter is converted into its diammonium salt, which reacts further only with difficulty.

Another process, in which solid naphthalene-1,8-dicarboxylic anhydride is reacted with gaseous ammonia under pressure at temperatures of 120° C. to 130° C. is described in German Offenlegungsschrift No. 2,137,242. This process can, however, only be carried out with high technical costs.

The process according to the invention for the preparation of naphthalene-1,8-dicarboximide which is optionally substituted in the naphthalene ring is characterized in that naphthalene-1,8-dicarboxylic anhydride which is optionally substituted in the naphthalene ring is reacted with an ammonium salt in an aqueous medium at a pH near to the neutral point, preferably a pH of 6.5 to 7.5, the reaction mixture is then acidified to a pH of 1 to 5, preferably 2.5 to 3.5, and the pH is subsequently again adjusted to a value near to the neutral point, preferably 6.5 to 7.5.

Surprisingly, the quality of the naphthalene-1,8-dicarboxylic anhydride employed is not decisive for the quality and yield of the imide.

The process is used in particular for the preparation of naphthalene-1,8-dicarboximides of the formula

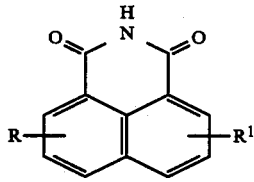

(I)

in which R and $R^1$ denote hydrogen, alkyl, preferably $C_1$-$C_4$-alkyl, for example methyl, ethyl, alkoxy, preferably $C_1$-$C_4$-alkoxy, for example methoxy or ethoxy, halogen, preferably chlorine or bromine, N,N-dialkylamino, preferably N,N-di-$C_1$-C-4-alkylamino, for example N,N-dimethylamino or N,N-diethylamino, and nitro.

The appropriately substituted naphthalene-1,8-dicarboxylic anhydrides or the unsubstituted anhydride are used as starting materials for the preparation of the compounds of the formula I.

These naphthalene-1,8-dicarboxylic anhydrides are known from the literature or can be prepared analogously to processes known from the literature.

The new process is used particularly preferentially for the preparation of unsubstituted naphthalene-1,8-dicarboximide.

The ammonium salts used are the ammonium salts of inorganic and organic acids, for example ammonium chloride, acetate, bisulphate, nitrate and carbonate, and, in particular, ammonium sulphate.

It is preferable to employ 1 to 1.5 equivalents of ammonium salt per mole of anhydride. It is particularly preferable to employ 0.52 to 0.75 mole, very particularly preferably 0.55 to 0.6 mole, of $(NH_4)_2SO_4$ per mole of anhydride. This corresponds to an excess of ammonia of about 10 to 20%, whereas according to the instructions from Chemisches Zentralblatt quoted above an excess of ammonia of 200% is required.

The process according to the invention is preferably carried out within the temperature range from 10° C. to the boiling point of the reaction mixture, particularly preferably at 70° to 100° C.

An alkali metal hydroxide or alkaline-earth metal hydroxide or a tertiary amine, for example triethylamine, in the form of aqueous solutions or suspensions, is customarily used to adjust the pH of the aqueous reaction mixture composed of anhydride and ammonium salt to a value near to the neutral point. The pH is preferably adjusted by means of sodium hydroxide solution.

A mineral acid, prefrably sulphuric acid, is used, in particular, to adjust the pH to a value from 1 to 4.

In order to complete the reaction, it is advisable to continue stirring for 0.5 to 3 hours, preferably 1 to 1.5 hours, at the pH near to the neutral point.

An embodiment of the process according to the invention consists in repeating the acidification to pH 1 to 4 and the adjustment of the pH to a value near to the neutral point several times, preferably once, twice or three times. This is particularly advisable if the anhydride employed is of an inferior quality, for example contaminated with naphthalic acid.

The reaction mixture is worked up in a customary manner, for example by filtration with suction, washing until neutral and drying.

Naphthalene-1,8-dicarboximides are obtained by the process according to the invention in a very high quality and in very high yields. The following examples serve to illustrate the invention; parts denote parts by weight and percentages denote percentages by weight.

EXAMPLE 1

148.7 parts of naphthalic anhydride (97.6% pure +2.0% of naphthalene-1,8-dicarboxylic acid) and 59.4 parts of ammonium sulphate are introduced into 750 parts of water, and the mixture is heated to 90° C. in the course of approximately 30 minutes. A pH of 3.0 to 3.5 is set up. Approximately 75 parts of 50% strength sodium hydroxide solution are then added dropwise as uniformly as possible in the course of 1 hour, so that the pH rises to 6.5 to 7.5. Stirring is continued for 1 hour at 90° C.

The pH is then adjusted to 3.0 by the dropwise addition of approximately 27 parts of 78% strength sulphuric acid, and the mixture is stirred for 30 minutes at 90° C.

A further 40 parts of 50% strength sodium hydroxide solution are then added dropwise in the course of 30 minutes in order to adjust the pH again to a value of 6.5 to 7.5.

After stirring has been continued for 2 hours at 90° C., the mixture is cooled to 60° C. and the product is filtered off with suction, washed with water until neutral and dried at 100° C.

144.9 parts of naphthalene-1,8-dicarboximide of 99.3% purity are obtained. This corresponds to a yield of pure material of 97.8% of theory.

EXAMPLE 2

148.7 parts of naphthalic anhydride (96.2% pure +0.9% of naphthalene-1,8-dicarboxylic acid) are reacted analogously to Example 1. In this case, however, the pH is adjusted to a value of 3.0 with sulphuric acid for a second time and then to a value of 6.5 to 7.5 with 50% strength sodium hydroxide solution.

142.9 parts of naphthalene-1,8-dicarboximide of 98.7% purity are obtained, which corresponds to a yield of pure material of 98% of theory.

EXAMPLE 3

The procedure is analogous to that of Example 1, 148.7 parts of naphthalic anhydride (90.4% pure +1.5% of naphthalene-1,8-dicarboxylic acid) being employed. The pH is, however, adjusted to a value of 3.0 and subsequently to a value of 6.5 to 7.5, 3 times in all.

136.4 parts of naphthalene-1,8-dicarboximide of 98.2% purity are obtained. This corresponds to a yield of pure material of 98.2% of theory.

We claim:

1. A process for the preparation of a napthalene-1,8-dicarboximide of the formula

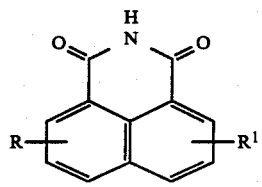

in which R and R$^1$ denotes hydrogen, alkyl, alkoxy, halogen, N,N-dialkylamino and nitro comprising reacting a napthalene-1,8-dicarboxylic anhydride of the formula

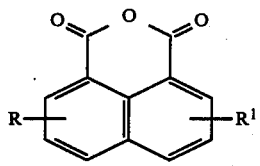

with an amonium salt in an aqueous medium at a pH of about 6.5 to 7.5, acidifying the reaction mixture to a pH of 1 to 4 and subsequently adjusting again the pH to a value of about 6.5 to 7.5.

2. Process according to claim 1 wherein the nephthalene-1,8-dicarboxamide is naphthalene-1,8-dicarboximide.

3. A process according to claim 1, wherein the amonium salt is amonium sulphate.

4. Process according to claim 1, wherein 1 to 1.5 equivalents of amonium salt are employed per mole of anhydride.

5. Process according to claim 1, wherein the reaction mixture is acidified to a pH of 2.5 to 3.5.

6. Process according to claim 1, wherein the acidification to pH 1 to 4 and the adjustment of the pH to a value of about 6.5 to 7.5 are repeated several times.

* * * * *